(12) United States Patent
Fang et al.

(10) Patent No.: US 7,511,807 B2
(45) Date of Patent: Mar. 31, 2009

(54) METHOD AND APPARATUS FOR DETECTION OF INCLUSION IN GLASS

(75) Inventors: Zhongping Fang, Singapore (SG); Tong Liu, Singapore (SG); Xiang Li, Singapore (SG); Ivan Reading, Singapore (SG)

(73) Assignee: Agency for Science, Technology and Research, Centros, Singapore (SG)

( * ) Notice: Subject to any disclaimer, the term of this patent is extended or adjusted under 35 U.S.C. 154(b) by 337 days.

(21) Appl. No.: 10/584,966

(22) PCT Filed: Dec. 30, 2003

(86) PCT No.: PCT/SG03/00294

§ 371 (c)(1),
(2), (4) Date: Jun. 30, 2006

(87) PCT Pub. No.: WO2005/064321

PCT Pub. Date: Jul. 14, 2005

(65) Prior Publication Data

US 2007/0165213 A1     Jul. 19, 2007

(51) Int. Cl.
*G01N 21/00*   (2006.01)
(52) U.S. Cl. .............. 356/239.7; 356/237.1; 356/239.8
(58) Field of Classification Search ......... 356/128–137, 356/237.1–241.6
See application file for complete search history.

(56) References Cited

U.S. PATENT DOCUMENTS

| | | | | |
|---|---|---|---|---|
| 3,737,665 A | * | 6/1973 | Nagae | 250/559.42 |
| 4,401,893 A | * | 8/1983 | Dehuysser | 250/559.49 |
| 4,645,337 A | * | 2/1987 | Obenreder | 356/128 |
| 4,652,745 A | * | 3/1987 | Zanardelli | 250/227.25 |
| 4,808,813 A | * | 2/1989 | Champetier | 356/338 |
| 5,117,120 A | * | 5/1992 | Margaliot et al. | 250/559.39 |
| 5,355,213 A | * | 10/1994 | Dotan | 356/239.7 |
| 5,790,247 A | * | 8/1998 | Henley et al. | 356/237.1 |
| 6,226,080 B1 | * | 5/2001 | Takeuchi et al. | 356/239.1 |
| 6,605,807 B2 | * | 8/2003 | Safai | 250/341.1 |
| 7,142,295 B2 | * | 11/2006 | Gahagan et al. | 356/237.2 |
| 7,292,332 B2 | * | 11/2007 | Gerstner et al. | 356/239.1 |
| 2002/0126290 A1 | * | 9/2002 | Naya | 356/445 |

FOREIGN PATENT DOCUMENTS

| | | | |
|---|---|---|---|
| DE | 10316707.2 | * | 4/2003 |
| JP | 06 082392 | | 3/1994 |
| JP | 2000 074848 | | 3/2000 |
| JP | 2001 305072 | | 10/2001 |

* cited by examiner

*Primary Examiner*—L. G Lauchman
*Assistant Examiner*—Jarreas C Underwood
(74) *Attorney, Agent, or Firm*—Fredrikson & Byron, PA (57) ABSTRACT

Inclusions in a transparent panel (5) are detected by placing a light transmissive interface (3) in contact with the panel (5), and transmitting a beam of light (1) through interface (3) into panel (5). Within the panel (5), the light beam (7) propagates along a path including total internal reflections at surfaces of panel (5). When the light beam (1) intercepts inclusions (10) or other defects at least some of it is scattered, and leaves the panel (5). This scattered light is then observed. Thus, a large zone of the panel (5) can be inspected, with light only being detected in the case that it arises from scattering by inclusions or other defects.

41 Claims, 7 Drawing Sheets

METHOD AND APPARATUS FOR DETECTION OF INCLUSION IN GLASS

RELATED APPLICATIONS

This application claims priority to International Application No. PCT/SG2003/000294 filed Dec. 30, 2003, the teachings of which are incorporated herein by reference.

FIELD OF THE INVENTION

The present invention relates to methods and apparatus for inspection of transparent panels, and in particular for detecting faults, such as "inclusions", in those panels. In particular, the invention relates to methods and apparatus which are suitable for use at a site where the transparent panel is located as a component of a building. However, the methods and apparatus may also have applications for quality control during a transparent panel manufacturing process.

BACKGROUND OF INVENTION

Transparent panels such as glass panels, especially panels of toughened glass, are widely employed in high-rise structures, and there is a need to inspect them to check for the presence faults. In particular, glass panels are subject to Nickel Sulphide (NiS) inclusions and other defects (faults). If such checks are not carried out, the Nickel Sulphide inclusions may cause the toughened glass to fracture, and the glass may shatter with potentially disastrous consequences, both for people inside the high-rise building, and on the ground beneath. Ideally, checks for inclusions and other faults should be performed during the manufacturing process for quality control (QC), and also in-situ once the panels are installed in the structures for quality assurance.

Several techniques are known for testing glass panels to observe inclusions.

A first of these is visual inspection, carried out using a microscope (e.g. a portable microscope), scanning the whole glass panel point-by-point manually, or automatically using a CCD (charge coupled devices) camera and image processing software based on a threshold. Unfortunately, this process is very slow, due to the limited field of view (FOV) and depth of focus (DOF) of the observation process. NiS is black/grey in colour and only reflects light weakly. NiS inclusions are therefore difficult to observe against the generally high intensity of background light caused by reflections and scattering of light due to surface contamination and scratches. Furthermore, many glass panels are printed with black dots to reduce the intensity of sunlight transmitted through them, and it is very difficult to observe the tiny dark inclusions in the shadow regions caused by the dots.

Secondly, there are photographic techniques in which a portion of the glass is photographed in controlled lighting conditions, and the image is magnified and visually examined to detect inclusions. Though the image is taken on site, the magnification and inspection are performed somewhere else. Thus, such techniques are not suitable for in-situ testing and are inconvenient even as a part of a QC mechanism.

Thirdly, there are techniques in which coherent laser light is directed at the front surface of a glass panel, and measurement are made of light scattered back towards the front surface by the inclusions, and also of light scattered forward by the inclusions and then reflected by the rear surface of the panel towards the front of the panel. Comparing these two signals makes it possible to determine the location, size and depth of the inclusion by signal analysis. However, in this technique only the area of the panel illuminated by the laser beam is measured. Furthermore, most of the energy of the laser is not utilized, and either completely penetrates the glass panel, or is reflected by the glass surfaces. Furthermore, contamination on either surface of the glass can cause light scattering, which induces noise in the measurement, and hence in the inclusion image obtained.

Fourthly, there is known a technique employing Raman spectroscopy, in which a laser is used as a light source and a nitrogen-controlled charge coupled device is used as the detector to obtain a Raman spectrum. By comparing the Raman spectrum of a measured glass panel with those of specific substances, the presence of inclusions such as NiS can be identified. However, present technology only allows this technique to be used in a laboratory because it requires critical control of implementation conditions. For this reason, it is better suited to measuring the composition of previously discovered inclusions, rather than for an initial inspection of a glass panel which may or may not include inclusions.

SUMMARY OF THE INVENTION

The present invention aims to provide a new and useful technique for detecting inclusions and other faults in transparent panels such as glass panels.

In particular the invention aims to provide a technique which is suitable for use in situ in a building, such as a high rise building, where the transparent panel is employed as a structural element. However, the invention is not limited in this respect, and other applications exist, such as part of a panel fabrication process.

In general terms, the invention proposes that a light-transmissive interface including a coupling material (which may be either entirely solid, semisolid (such as gel or jelly), liquid, or even gas) is placed in contact with the transparent panel, and that a beam of light is transmitted through the interface into the panel. In the panel, the condition of total internal reflection is fulfilled with the selected coupling material and designed geometric shape and incident angle. The light beam is total internal reflected at the surfaces of the panel and propagates within the panel. When the light beam intercepts inclusions or other defects at least some of it is scattered, and leaves the panel. This scattered light is then observed.

Because of total internal reflection, light beam can travel a long distance within the panel. The method thus makes it possible to examine a relatively large area of the panel at a single time in contrast to the methods described above.

The scattering light caused by the inclusion or other faults is very easy to be observed or detected, because the scattered light makes the defaults and inclusions stand out like stars. Therefore, no magnification of an image is necessary, as in the photographic technique, and no complex instrumentation is required as in Raman spectroscopy. Indeed, the inclusions will often be visible to the naked eye, although cameras may also be used within the scope of the invention.

These features mean that the present invention is particularly suitable for use in situ examining a panel which is fixed in position within a building or other construction. In contrast to the Raman techniques discussed above, the existence and location of the inclusions is typically obtained, rather than their chemical structure.

Furthermore, in contrast to the laser scattering technique described above, a much larger area of the panel ("field of view") can be simultaneously tested than simply the area which is illuminated directly by the beam. Also, because of the total internal refraction, all of the light energy will be trapped inside of the panel. Only when the light strikes on an inclusion, the scattered light exits the path and thereby exits the panel. That is, the input light is used highly efficiently. The high efficiency of using the input light energy is advantageous for the two reasons. Firstly, most of the transparent panels, such as the toughed glass panels have a high absorption coefficient. Without the efficient use of the light energy, even with a high power light source, the field of view will still be very small, which results in a very slow inspection speed. Secondly, without the light leakage, the contrast of the images is high; all the defects are bright points like stars against the dark background of the other area of the panel.

As noted above, many transparent panels include a printed pattern, such as black dots on one side of the panel, that results in great difficulty for known inspection methods. However, a method according to the present invention may still work very well under these circumstances.

Most preferably, the panel is a glass panel, but the invention can also usefully be used for panels of other transparent material, such as a transparent polymer, which is capable to providing total internal reflection to a beam of light propagating within it.

Also, although as noted above, the invention is particularly useful for detecting inclusions or other internal faults in the panel (e.g. cracks, air bubbles and other foreign substance), it may also be used for detecting surface faults such as scratches or dents.

Specifically, one expression of the invention is a method for detecting faults, such as inclusions, within a transparent panel which is located in an ambient atmosphere, the method comprising:

directing light from a light source into an interface in contact with the glass panel, the interface including one or more interface elements having a refractive index higher than the ambient atmosphere, at least some of the light passing through the interface into the glass panel and propagating within the glass panel along a path where total internal reflection (TIR) is realized at the surface of the glass panel; and observing at least some of any of light scattered by the faults and exiting the panel.

An alternative expression of the invention is an apparatus for detecting faults, such as inclusions, within a transparent panel which is located in an ambient atmosphere, the apparatus comprising:

a light source;

an interface including one or more interface elements having a refractive index higher than the ambient atmosphere and transparent to light generated by the light source; and light source support means for locating the light source in a positional relationship to the interface such that when the interface is contacting the panel, light generated by the light source is transmitted through the interface into the panel and propagates within the panel along a path where total internal reflection is realized at the surface of the panel.

BRIEF DESCRIPTION OF THE FIGURES

Preferred features of the invention will now be described, for the sake of illustration only, with reference to the following figures in which:

FIG. 4, which is composed of FIGS. 4(a) to 4(c), shows schematically the interaction of an NiS inclusion or other fault with light in the embodiment of FIG. 2, and experimental results obtained by such a technique;

FIG. 5, which is composed of FIGS. 5(a) to 5(c), explains principles underlying embodiments of the invention;

FIG. 9, which is composed of FIGS. 9(a) to 9(f), show a further embodiment of the invention, and three variants of it;

FIG. 10, which is composed of FIGS. 10(a) to 10(c), shows schematically three forms of the invention;

FIG. 11, which is composed of FIGS. 11(a) and 11(b) shows a further embodiment of the invention.

DETAILED DESCRIPTION OF THE EMBODIMENTS

Figure 1:
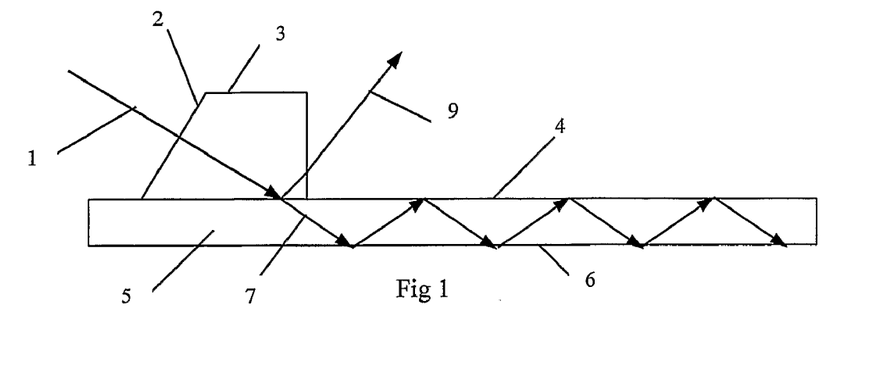
FIG. 1 shows the principle underlying an embodiment of the invention.

Referring firstly to FIG. 1, the overall structure of an embodiment of the invention is illustrated.

A beam of light 1 emitted by a light source (not shown) is directed into an interface consisting of an interface element 3 which is in contact with a glass panel 5 to be investigated. The interface element 3 has a generally prism-shaped cross-section when viewed in the direction into the page (i.e. it includes a flat surface 2 which is inclined with respect to the surfaces 4, 6 of the glass panel 5 when the interface 3 rests on the panel 5). The beam 1 passes through the interface element 3, and due to the relative refractive indices of the interface element 3 and glass panel 5 (discussed below) a portion 7 of the beam enters the panel 5 and a portion 9 of the beam is reflected back.

The beam 7 travels in a zig-zag path through the glass panel 5. It meets the surfaces 4, 6 of the glass panel 5 at locations where the interface element 3 is not present, and at an angle to the surfaces 4,6 such that it is totally internally reflected. This means that—unless the beam encounters a fault, such as an inclusion—it will propagate along the panel until it encounters the end of the panel or is absorbed by the material of panel. The beam 1 and 7 is ideal line which is used to show the principle—how the light is coupled to panel and how the light is total internal reflected in the panel The embodiment of FIG. 1 is shown in a different view in FIG. 2. A beam of light 11 is generated by a light source 12 which is so positioned that the beam 11 is directed at a interface element 3 located on the surface 4 of a glass panel 5. The difference between this view and that of FIG. 1 is that the light source 12 is a fibre bundle which generates a light beam 11 with a little divergence. Thus, the internal portion 17 of the glass panel 5 which is illuminated is not limited to a single line, but rather includes the entire volume shown shaded. However, the entire angular range of the beam components of the beam 1 is preferably sufficiently narrow that all the beam components of the light beam extending within the panel 5 meet the surfaces 4, 6 at angles such that the total internal reflection is realized Note that in the embodiment of FIG. 1 and 2, the interface element 3 can be provided as a body of flexible (i.e. elastic) material, so that it is able to conform to any roughness of the glass panel 5, thereby provided an increased contact area (i.e. a reduced number of air gaps between the interface element 3 and the glass panel 5). Silicon rubber is a suitable material for the interface element 3.

Figure 3:
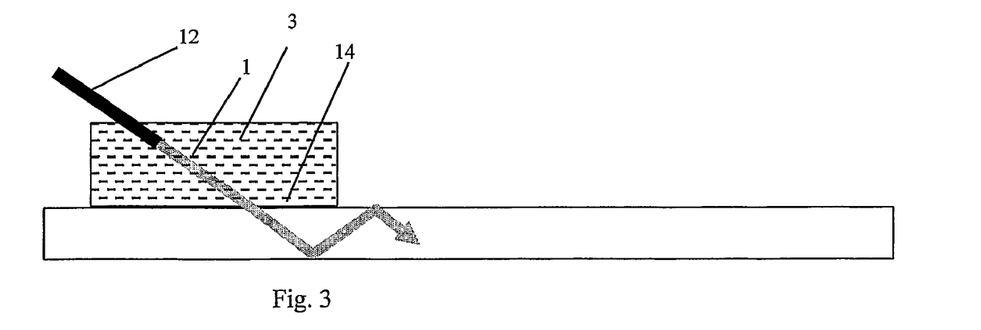
FIG. 3 shows a second embodiment of the invention.

Alternatively, or additionally, the interface can include a liquid layer between the interface element 3 and the glass panel 5. The liquid may for example be water. This too increases the total contact area (i.e. reduces the possibility of air gaps between the interface and the glass panel 5). Furthermore the liquid may lubricate the contact between the interface element 3 and the glass panel 5, thereby making it easier to move the interface element 3 when it is desired to inspect a different area of the glass panel 5. This possibility is illustrated in a second embodiment of the invention shown in FIG. 3. In this case the light source 12 is embedded in the interface element 3 (which does not have a prism-shaped cross-section). A layer 14 of liquid is present between the interface element 3 and the glass panel 5. A mechanism (not shown) can be provided for refreshing this liquid layer 9 (e.g. a reservoir and a pump for moving liquid from the reservoir from the pump). Water is preferred as the liquid, due to its cheapness and environmental reasons. Note that the embodiment of FIG. 3 is particularly suitable for use in quality control as part of a glass panel production line.

Figure 4A:
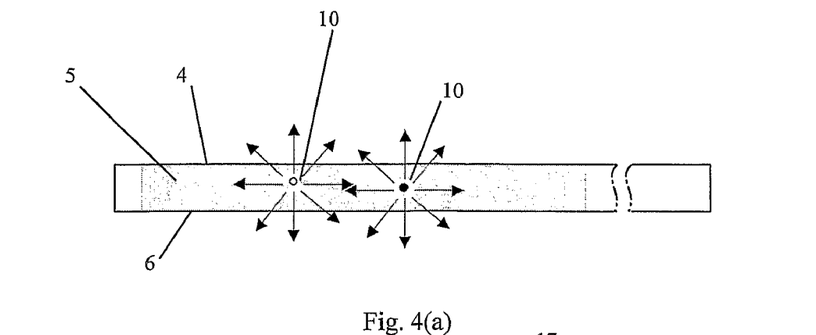
Figure 4B:
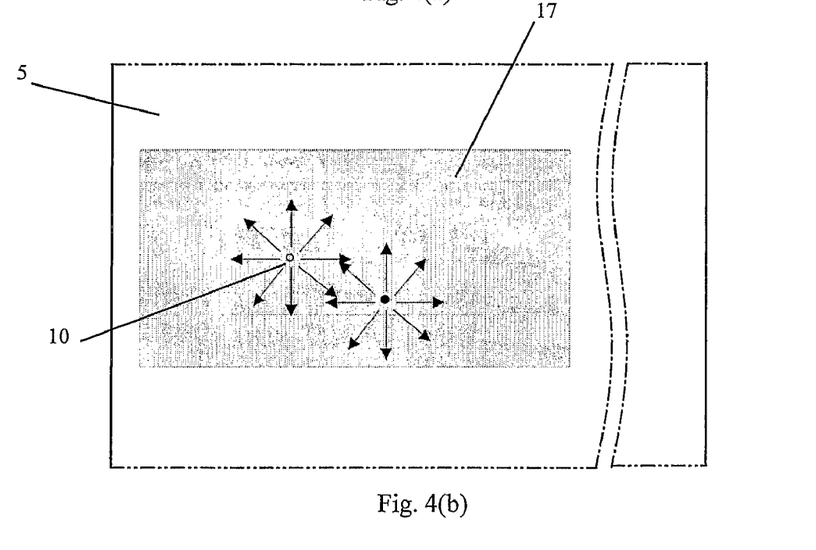
Figure 4C:
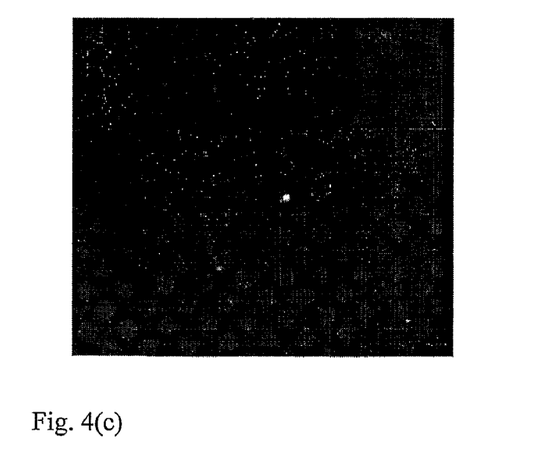

FIGS. 4(*a*) and 4(*b*) show schematically the interaction of the beam 17 of light with an inclusion 10 in the panel 5. FIG. 4(*a*) is a view from one edge of the panel, while FIG. 4(*b*) is a view looking towards one of the surfaces 4, 6 of the panel. When the glass is illuminated, the inclusions 10 scatter the incident light. The scattered light is easily observed or detected, by an observer, for example an observer on either side 4 or 6 of the panel 5. FIG. 4(*c*) is an experimental observation of this phenomenon, showing how the light scattered by an inclusion appears to such an observer as a bright spot on the panel. The same visual effect would be achieved in the situation of FIG. 1, in the case that the inclusion 10 intersects with the beam 7. Note also, that within the scope of the invention, the observer may be on either of the sides 4, 6 of the panel 5, since the inclusion 10 scatters the light in all directions.

Figure 2:
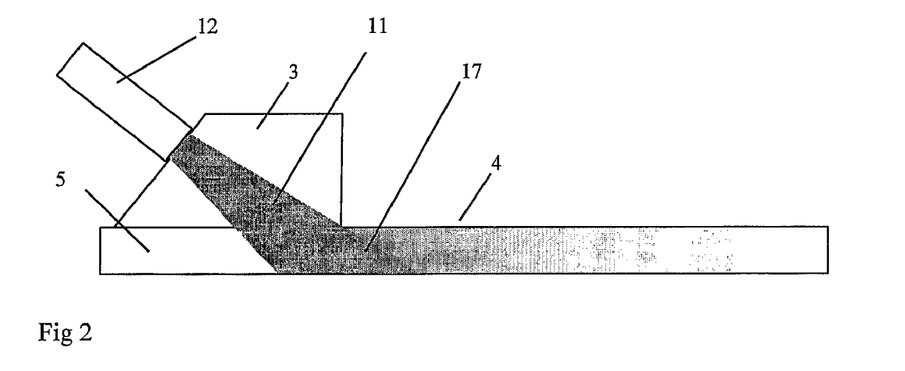
FIG. 2 shows schematically a second view of the embodiment of FIG. 1 in which the light source is a fibre bundle.
Figure 5A:
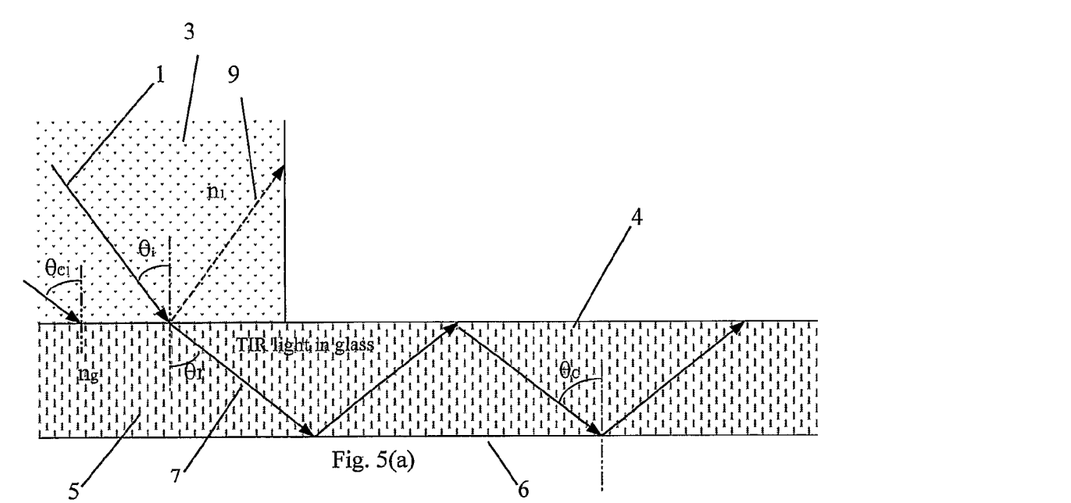

FIG. 5 illustrates the conditions under which there is total internal reflection of the light beam 7 in the embodiment of FIG. 1 (or equivalently, one of the beam components of the diverging beam of FIG. 2). FIG. 5(*a*) shows a case in which the interface element 3 is selected such that its refractive index, $n_1$, is greater than that $n_g$ of the glass panel 5. As shown in FIG. 5(*a*), the incident angle of the beam 1 on the glass is denoted by $\theta_i$, and, following the refraction, the direction in which the beam 7 propagates is denoted by $\theta_r$. When the beam 7 travels inside the glass and encounters either surface 4 or 6 of the glass in the air, the incident angle, at which the TIR occurs, is the critical angle, which is denoted as $\theta_c$.

Correspondingly, the critical angle in the case that the beam 1 meets the surface 4 at a location where the surface 4 is in contact with the interface element 3 is denoted by $\theta_{c1}$. The incident angle when θr=θc is denoted by θi'.

According to Snell's law of refraction, it can be derived that:

$\theta_i'=\sin^{-1}(1/n_1)$ $\theta_{c1}=\sin^{-1}(n_g/n_i)$

When $\theta_i'<\theta_i<\theta_{c1}$, the light will be directed into the glass and propagate inside the glass with TIR.

Figure 5B:
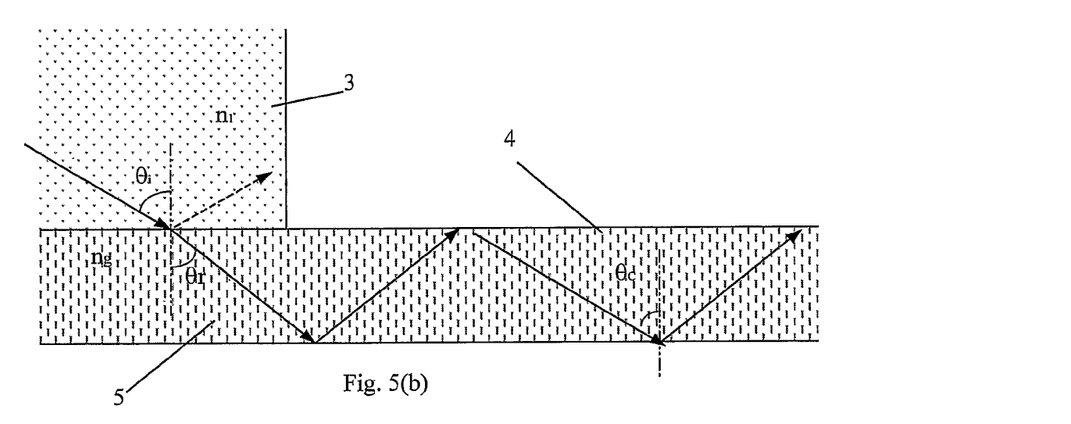

An alternative case, illustrated in FIG. 5(*b*), is that $n_1 \leq n_g$. In this case, when $\theta_i \geq \theta_i'=\sin^{-1}(1/n_1)$, the light will be directed into the glass panel and propagate inside the glass with TIR.

Figure 5C:
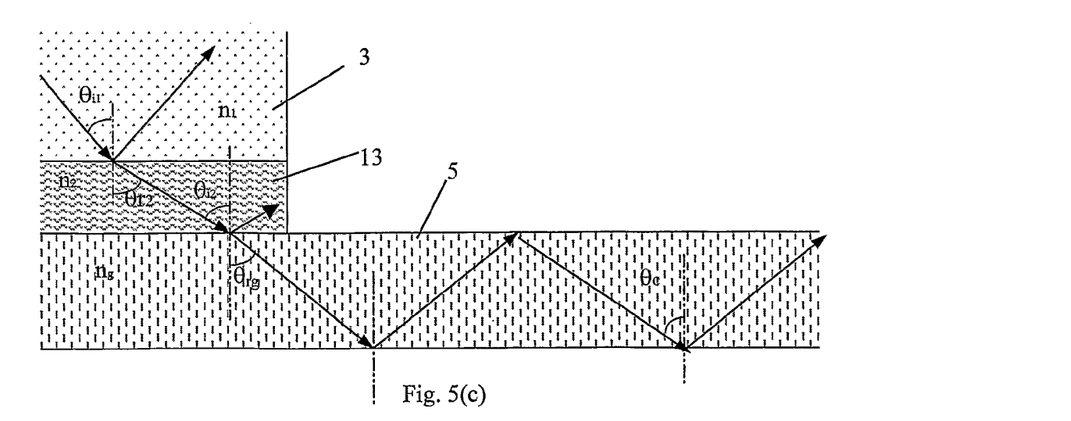

A third case, within the scope of the invention, is that more than the interface may include more than one interface element, or when the interface includes an interface element 3 and a layer of liquid 13. These possibilities are shown in FIG. 5(*c*). This situation can be analyzed layer-by-layer according to their refractive index following the above 2 steps. The following conditions are given as an example, $n_1>n_2$, $n_2<n_g$, $n_1<n_g$, where $n_1$, $n_2$ and $n_g$ are the refractive index of the media 3, 13 and glass. The relevant parameters are defined as follows, with reference to FIG. 5(*c*):

$\theta_{i1}, \theta_{i2}$—incident angles,
$\theta_{r2}, \theta_{rg}$—refractive angles,
$\theta_{i1}', \theta_{i2}'$—incident angles when $\theta_{rg}=\theta_c$,
θc—critical angle from glass to air,
$\theta_{c1}$—critical angle from interface element 3 to liquid layer 13, According to Snell's law,
it can be derived that:

$\theta_1'=\sin^{-1}(1/n_1)$ $\theta_{c1}=\sin^{-1}(n_2/n_1)$

When $\theta_{c1}>\theta_{i1}>\theta_1'$, the light can reach the glass panel 5 through prism 3 and layer 13, and will propagate in the glass panel 5 with TIR at its surfaces.

At this point we will consider the energy lost caused by reflections at the boundary of the media 3, 13. According to Fresnel's formulae, the parallel and perpendicular reflectivities are, $$R_{\|} = \frac{\tan^2(\theta_i - \theta_r)}{\tan^2(\theta_i + \theta_r)}$$

$$R_{\perp} = \frac{\sin^2(\theta_i - \theta_r)}{\sin^2(\theta_i + \theta_r)}$$

When $\theta_i$ is close to $\theta_r$, $R_{II}$ and $R_{\perp}$ are near to zero. This means when the 2 refractive indexes are close, the reflectivity is smaller. When the two refractive indices are the same, the reflectivity is zero.

To improve the light coupling efficiency, a deformable solid interface element with refractive index approximately equal to toughened glass can be used. The refractive index of toughened glass is approximately 1.5 in the visible spectrum. For this reason, silicon rubber, which has refractive index of approximately 1.4 in the visible spectrum, may be selected as one of the interface elements 3.

Figure 6:
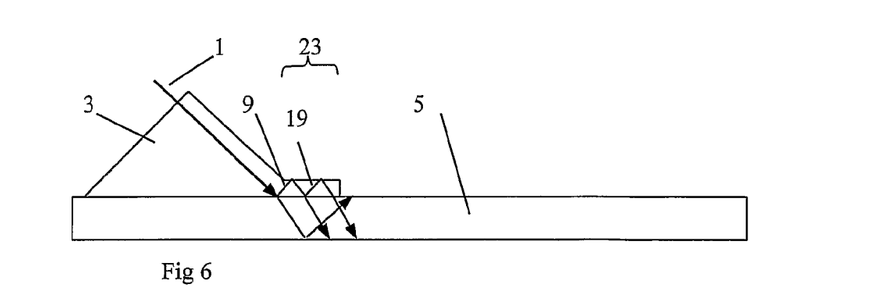
FIG. 6 shows a third embodiment of the invention.

FIG. 6 shows a third embodiment of the invention. This embodiment is motivated by the observation that, as noted above, in the first and second embodiments a portion 9 of the incident light will be reflected at the surface 4 of the panel as the beam 9. The larger the incident angle, the higher the amount of light reflected. Thus, in the third embodiment an extended foot section 23 is provided as part of the generally prism-shaped interface element 3. The light beam 9 is reflected back toward the glass panel 5. If any light is further reflected back from the surface 4 once again, as beam 19, it may be reflected back towards the glass panel 5 again by the foot section 23.

Figure 7:
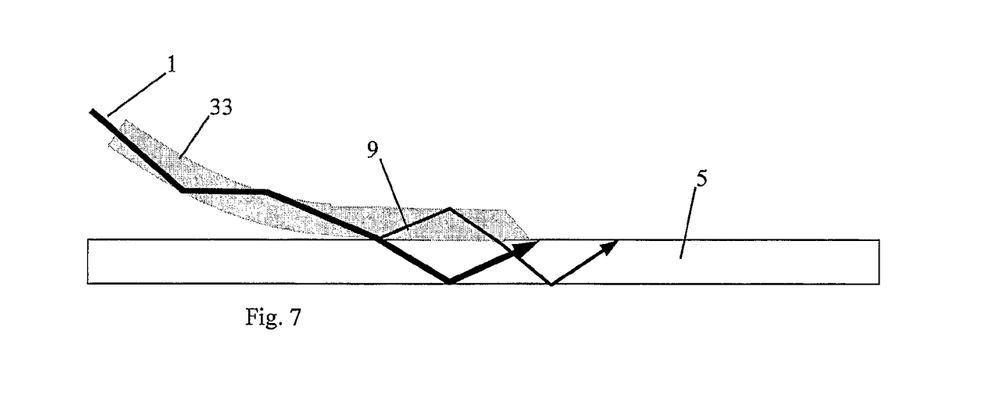
FIG. 7 shows a fourth embodiment of the invention.

Whereas in the embodiments described above, the interface element 3 was generally prism-shaped in cross-section, it may alternatively be provided as a flexible sheet of deformable material (e.g. silicon rubber). Such a fourth embodiment of the invention is shown in FIG. 7. The incident light beam 1 from the light source (not shown) enters one end of the interface element 33, and then propagates within it as a beam which is total internal reflected whenever it encounters the faces of the sheet 33 at a location where that surface is not in contact with the glass panel (in a way similar to the propagation of the light within the glass panel 5 in the embodiments described above).

When the beam 1 reaches a part of the interface element 33 which is touching the glass panel 5, the conditions for TIR no longer apply, because the difference between the refractive indices of the interface element 33 and the glass panel 5 is too low. Thus, the light passes into the glass. When the refractive indices of the interface element 33 and the glass panel 5 are very close, the light coupling efficiency is high.

Figure 8:
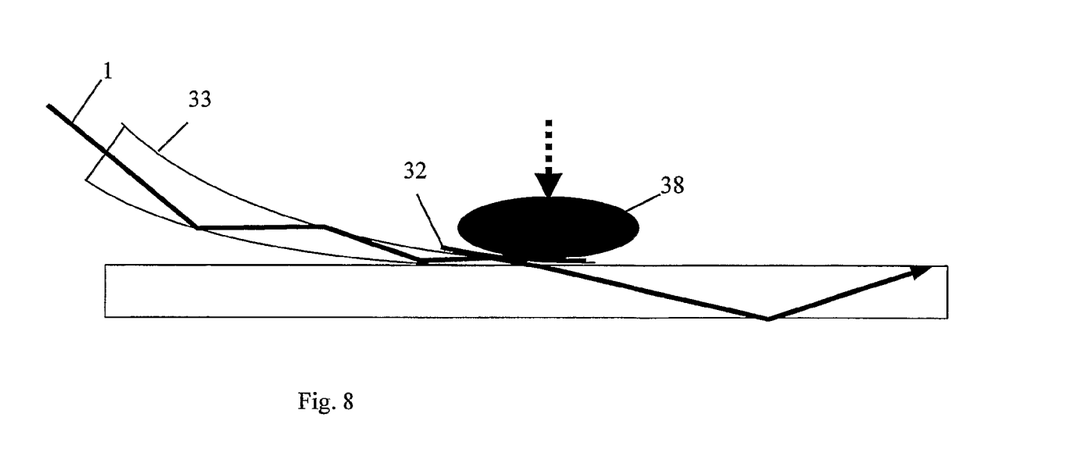
FIG. 8 shows a technique for using the embodiment of FIG. 7.

As shown in FIG. 8, optionally an object (e.g. airbag 38) can be used to press the interface element 33 into full contact with the glass. A downward force shown by the dashed arrow can be applied to the airbag 38.

Optionally, to prevent, or at least reduce, the leakage of light, a reflective coating/sheet 32 can be added on the topside of the interface element 33.

In another embodiment, the role of the interface element is performed by a roller 43, as shown in FIG. 9. FIG. 9(a) is a top view of embodiment, looking towards the surface 4 of the glass panel 5. FIG. 9(b) is a view of the embodiment from a location at the edge of the panel 5 (specifically, at the bottom of FIG. 9(a)). FIG. 9(c) is the embodiment seen from a position at the right of FIG. 9(a). The roller 43 has an outer profile which is cylindrical, and its longitudinal axis is parallel to the surface of the glass panel 5. The axis is parallel to the left-right direction in FIG. 9(a). Preferably, at least one end of the roller 3 is not flat, but instead has a profile which is shown by the dashed lines in FIG. 9(b): that is, it includes a flat portion 431 and a frusto-conical portion 433, both being rotationally symmetric about the longitudinal axis of the roller 43.

A light beam 1 from a light source (not shown) is incident on the lower part of the portion 433 of the end of the roller 43. Thus, this part of the portion 433 acts as a prism (cf. the prism-shaped interface element 3 above). The light beam 1 passes through the roller into the glass panel 5. Preferably, the roller is made of flexible material such as silicone rubber, so that the contact area between it and the glass panel is not just a very narrow line parallel to the axis of the roller 43, but includes an extension in the perpendicular direction (i.e. the up-down direction in FIG. 9(a)). Thus, a strip zone 47 inside the glass will be illuminated. Those inclusions which, at any moment are within this strip 47 will scatter light out of the major surfaces 4,6 of the panel 5, and some of this scattered light is observed and measured. The whole glass panel 5 can be inspected by rolling the interface element 43 about its axis across the surface 4, thus moving the strip 47 (e.g. in the direction indicated by the arrows in FIG. 9(a) and 9(c)).

Figure 9A:
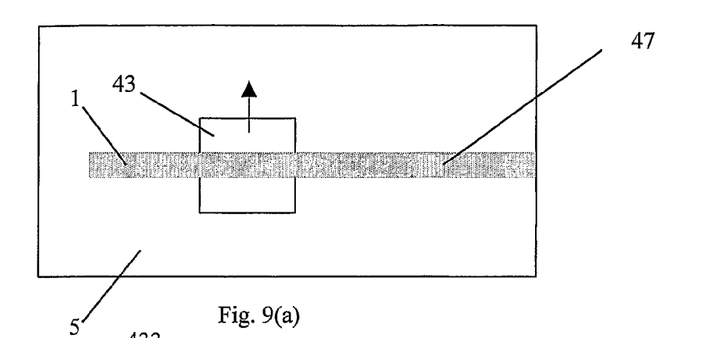
Figure 9B:
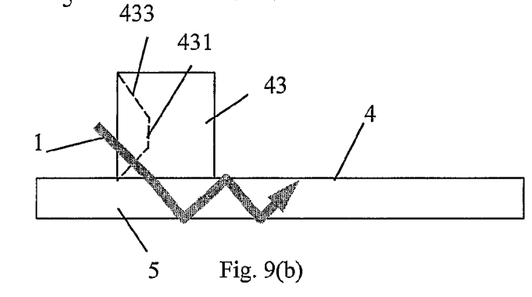
Figure 9C:
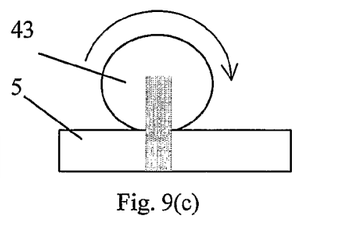
Figure 9D:
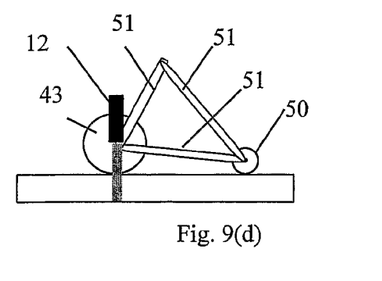
Figure 9E:
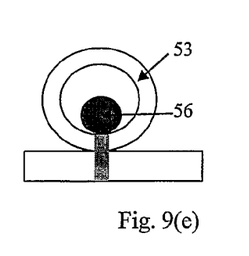
Figure 9F:
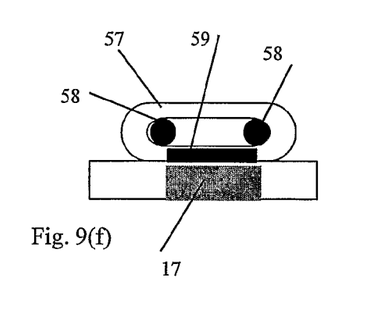

FIGS. 9(d) to 9(f) show variants of the previous embodiment. In all cases, the variant is shown viewed in a direction corresponding to FIG. 9(c).

Referring to FIG. 9(d), in this variant of embodiment FIGS. 9(a) to 9(c) the light source 12 is fixedly mounted in relation to the roller 43. Compared to the arrangement of FIGS. 9(a) to 9(c), an additional roller 50 is provided connected to the roller 43 by a rigid structure (e.g. a triangle of rods 51). Thus, the roller 43 can be rolled over the glass panel 5 while the light source 12 is maintained pointing in a fixed direction.

Turning to FIG. 9(e) another variant is shown of the embodiment in FIGS. 9(a) to 9(c). In this case, the interface element 53 may be thought of as the outer portion of the roller 43 (including the frustoconical portions 433), but the roller 53 is now hollow (i.e. the element 53 differs from element 43 of FIG. 9(a) by the central cylindrical portion having areas 431 at its ends being removed). Inside element 53 is another body 56 including the light source. Again, the roller 43 rolls on the surface of the glass, and light source is supported to keep pointing at the glass panel 5. The body 56 remains at a fixed distance and orientation relative to the glass panel 5.

Turning to FIG. 9(f), yet another embodiment which is a variant of the one of FIGS. 9(a) to (c) is shown. This embodiment has a flexible (e.g. silicone rubber) ring 57 which is maintained in an elongate lozenge-like shape by two internal members 58, with a flat region between them. A light source 59 generates light in a line, extending for a greater distance in the left-right direction than in the other embodiments of FIGS. 9(a) to (e), so as to illuminate a wider zone 17 (e.g. more than half of the substantially flat region at the bottom of the ring 57).

Figure 10A:
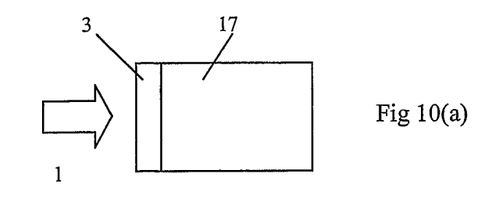
Figure 10B:
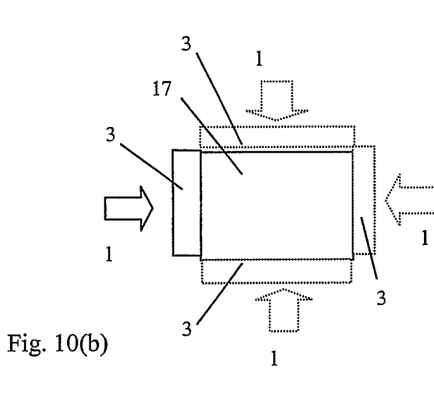

In the embodiments described above, the inclusion is illuminated by a light source to one side only, as indicated schematically, looking towards the panel, in FIG. 10(a), where a light beam 1 enters a glass panel through interface element 3 and illuminates a region 17 of the glass panel. However the invention is not limited in this respect, and within the scope of the invention the inclusion may be illuminated from any number of different directions, e.g. one, two, three or four. For example, FIG. 10(b) shows schematically an arrangement in which an area 17 of the glass panel 5 is illuminated from four different directions using light beams I generated by four respective light sources (not shown) which enter the glass panel 5 through respective interface elements 3. The elements of FIG. 10(b) which are not present in FIG. 10(a) are shown dashed.

Figure 10C:
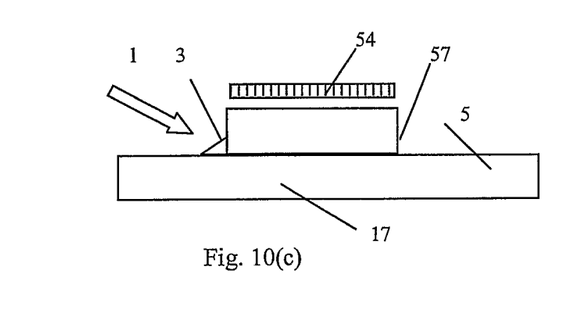

In any of the embodiments described above, the detection of the light scattered by the inclusions can be performed by the human eye (if the light is in the visible range). However, alternatively the detection can be performed by a camera 54 or any other detector which is sensitive to the light employed. A possible such arrangement is shown in FIG. 10(c). The light scattered in the illuminated region 17 of the panel 5 passes through a space surrounded by a dark box 57 (used to block the background light) to the detector 54. The dark box 57 is used to enhance the contrast of the image. It permits the scattered light to enter and leave it perpendicular to its major surfaces (i.e. its top and bottom surfaces) for easy detection or observation, but it can prevent ambient light from outside.

In embodiments of the invention which include one or more cameras, the output of those cameras may be fed to an automated image analysis system implemented by a computer device. The image analysis system may be programmed simply to record the number of inclusions identified. However, in more sophisticated embodiments it is programmed to discriminate different types of faults, such as distinguishing air bubbles from solid inclusions based on one or more of their size, shape and reflectivity.

FIG. 11 shows a further embodiment of the invention in which there are two light sources (not shown) arranged to generate light beams 1a, 1b having components in the plane of the glass panel 5 which propagate in perpendicular directions, and, for each light source, a respective interface element 63a, 63b (which may be any of the interface elements described above, with or without the liquid layer) and a respective detector 64a, 64b. A given inclusion 60 thus scatters light which is detected by the detectors 64a, 64b when the corresponding zones of light include the inclusion. Thus, the position of the inclusion 60 in each of the perpendicular directions can be determined.

Figure 11A:
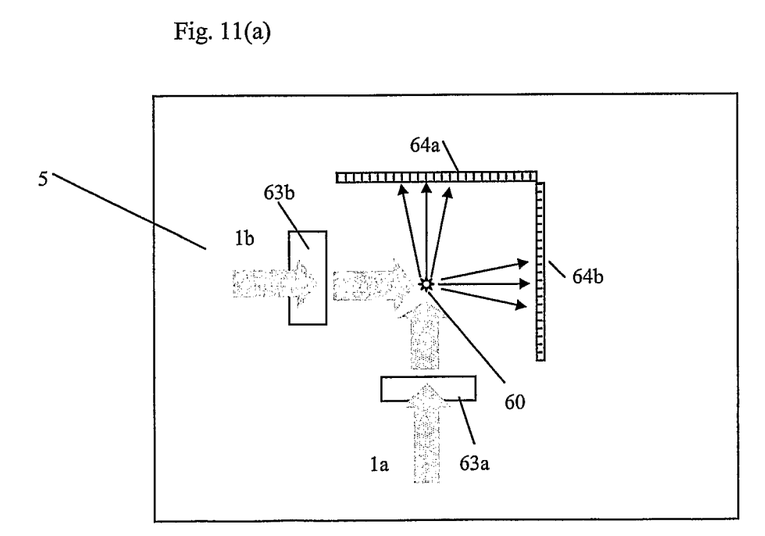
Figure 11B:
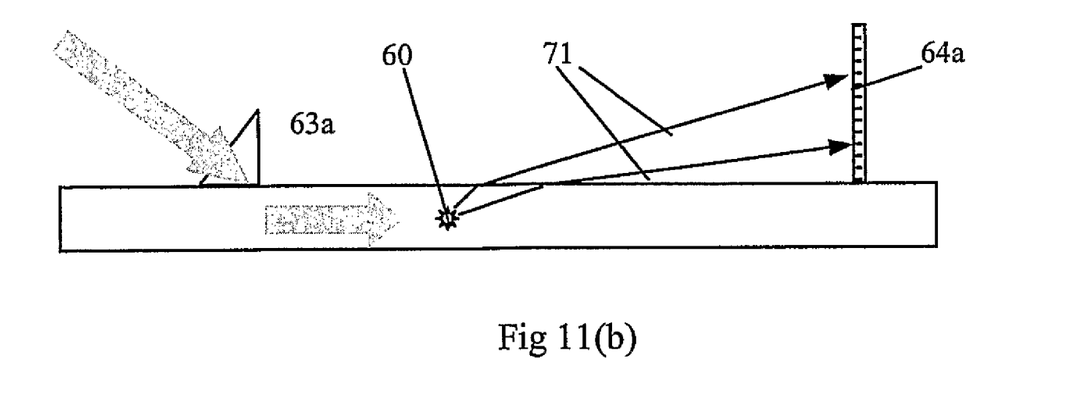

FIG. 11(b) is the section view of FIG. 11(a). A beam of light (e.g. the light beam 1a) which is introduced into the glass panel 5 via an interface element 63a generates scattered light which propagates as beams 71 towards detector 64a. Based on a knowledge of the position of the inclusion 60 in the direction which is left-to-right in FIG. 11(b) (this knowledge is obtained using the other detector 64b, as described above in relation to FIG. 11), the three dimensional location of the inclusion can be calculated.

Note that all of the embodiments described above will continue to operate reasonably well even if the glass panel 5 includes regions at which its surface is covered, e.g. by dots, as is typically for many panels of glass in common use, e.g. as construction elements of buildings.

Although the invention has been explained above in relation to particular embodiments, many variations are possible within the scope of the invention as will be clear to a skilled reader.

For example, although in the embodiments above the panel 5 is a glass panel, it may alternatively be a transparent panel of another transparent material which is capable of causing a total internal reflection to a beam of light which encounters a surface of the panel with an angle of incidence within an appropriate range.

Also, although the description above is in terms of detecting faults which are inclusions, the invention is applicable to any other faults which cause scattering of light, in particular faults within the panel (such as cracks) or faults on the surface of the panel, e.g. scatches or dents. Often these faults can be distinguished from each other visually by an operator, but alternatively the can be distinguished computationally by the automated image analysis system.

Furthermore, although the description above refers to the beam 1 as being "light", this is not intended to imply that the light is in the visible range. Rather, the term "light" should be understood also to include electromagnetic in other frequency ranges, such as IR radiation and UV radiation.

Similarly, the light source 12 may be any of a number of possible light sources, such as a fiber bundle, a line-type light source, a bulb or filament, e.g. of tungsten.

The invention claimed is:

1. A method for detecting faults, such as inclusions, within a transparent panel which is located in an ambient atmosphere, the method comprising:
   directing light from a light source into an interface in contact with the transparent panel, the interface including one or more interface elements having a body of flexible material, which is pressed against the panel, whereby the body is deformed to increase the area of the panel with which it is in contact, and further having a refractive index higher than the ambient atmosphere, at least some of the light passing through the interface into the transparent panel and propagating within the transparent panel along a path where total internal reflection is realized at surfaces of the transparent panel; and
   observing the light scattered by the faults and exiting the panel.

2. A method according to claim 1 in which the body is composed of silicone rubber.

3. A method according to claim 1 in which the interface includes a plurality of the interface elements, each having a refractive index greater than the ambient medium.

4. A method according to claim 1 in which the interface further includes a liquid coupling layer interposed between the panel and the one or more interface elements.

5. A method according to claim 4 in which the liquid coupling layer is substantially composed of water.

6. A method according to claim 1 in which the one or more interface elements include at least one interface element including a portion which has a generally prism-shaped cross-section when viewed in a direction perpendicular to the light path.

7. A method according to claim 1 in which the interface and light source are moved over the panel to vary the portion of the panel which is illuminated by the light.

8. A method according to claim 7 in which the interface includes at least one interface element which rolls over the surface of the panel when the interface is moved.

9. A method according to claim 8 in which the interface which rolls has circular cross-section when viewed in a direction perpendicular to the light path.

10. A method according to claim 8 in which the interface element which rolls is maintained in a configuration which is elongate in the direction in which it rolls, the configuration including a substantially flat portion facing the panel, the light source providing the light along the length of the substantially flat portion.

11. A method according to claim 9 in which the light source moves in fixed positional relationship with the interface element having a circular cross-section.

12. A method according to claim 1 in which the interface includes at least one interface element which is a flexible wave guide.

13. A method according to claim 1 in which at least a portion of the surface of the interface, other than the portions through which the light beam enters the interface and the portion of the interface which contacts the panel, has a coating for reflecting light.

14. A method according to claim 1 in which the ambient medium is air.

15. A method according to claim 1 in which the scattered light is observed by a human operator.

16. A method according to claim 1 in which the scattered light is observed by one of more electronic detectors or cameras.

17. A method according to claim 16 in which the one or more electronic detectors or cameras are electronically coupled to an automated image analysis system.

18. A method according to claim 17 in which the automated image analysis system determines from the output of the one or more detectors or cameras the type of fault which scattered the light.

19. A method according to claim 18 in which the automated image analysis system discriminates the defects, air bubbles and solid inclusions etc based on their size, shape and reflectivity.

20. A method according to claim 16 in which there are a plurality of the cameras and a corresponding plurality of the light sources, the cameras being arranged to observe the illuminated region of the panel from different directions.

21. A method according to claim 20 in which the one or more electronic detectors or cameras are electronically coupled to an automated image analysis system, and in which the automated image analysis system determines the position of a detected inclusion in the thickness direction of the panel.

22. A method according to claim 1 in which the transparent panel is glass.

23. A method according to claim 1 in which the transparent panel is a transparent polymer.

24. An apparatus for detecting faults, such as inclusions, within a transparent panel which is located in an ambient atmosphere, the apparatus comprising:
   a light source;
   an interface including one or more interface elements having a body of flexible material, whereby upon pressing the body against the panel the body is deformed to conform to the surface of the panel, and further having a refractive index higher than the ambient atmosphere and transparent to light generated by the light source;
   light source support means for locating the light source in a positional relationship to the interface such that when the interface is contacting the panel, light generated by the light source is transmitted through the interface into the panel and propagates within the panel along a path where total internal reflection is realized at surfaces of the panel; and a detector for detecting light scattered by the faults and exiting the panel.

25. An apparatus according to claim 24 in which the body is composed of silicone rubber.

26. An apparatus according to claim 24 in which the interface includes a plurality of the interface elements, each having a refractive index greater than the ambient medium.

27. An apparatus according to claim 24 further including means for providing the interface with a liquid coupling layer interposed between the panel and the one or more interface elements.

28. An apparatus according to claim 24 in which the one or more interface elements include at least one interface element including a portion which has a generally prism-shaped cross-section when viewed in a direction perpendicular to the path of light generated by the light source.

29. An apparatus according to claim 24 in which the interface is adapted to be moved over the panel to vary the portion of the panel which is illuminated by the light.

30. An apparatus according to claim 29 in which the interface includes at least one interface element adapted to roll over the surface of the panel when the interface is moved.

31. An apparatus according to claim 30 in which the interface element adapted to roll has a circular cross-section.

32. An apparatus according to claim 30 further including means for maintaining the interface element which is adapted to roll in a configuration which is elongate in the direction in which it rolls and which includes a substantially flat portion, the light source being arranged to provide the light along the substantially flat portion.

33. A method according to claim 29 in which the light source support means is arranged, as the interface moves over the surface of the panel, to move the light source maintaining fixed positional relationship with the interface.

34. An apparatus according to claim 24 in which the interface includes at least one interface element which is a flexible wave guide sheet.

35. An apparatus according to claim 24 in which at least a portion of the surface of the interface, other than the portions through which the light beam enters the interface and the portion of the interface which contacts the panel, has a coating for reflecting light.

36. An apparatus according to claim 24 further including one or more electronic detectors for detecting the scattered light.

37. An apparatus according to claim 36 further including an automated image analysis system arranged to receive data output by the one or more electronic detectors.

38. An apparatus according to claim 37 in which the automated image analysis system is arranged to determine from the output of the one or more detectors the type of fault which scattered the light.

39. An apparatus according to claim 38 in which the automated image analysis system is arranged to discriminate air bubbles from solid inclusions based on their size, shape and/or reflectivity.

40. An apparatus according to claim 36 in which there are a plurality of the cameras and a corresponding plurality of the light sources, the cameras being arranged to observe the illuminated region of the panel from different directions.

41. An apparatus according to claim 40 further including an automated image analysis system arranged to receive data output by the one or more electronic detectors, and in which the automated image analysis system is arranged to determine the position of a detected inclusion in the thickness direction of the panel.

* * * * *